(12) United States Patent
Richard et al.

(10) Patent No.: US 8,865,791 B2
(45) Date of Patent: Oct. 21, 2014

(54) ENDODONTIC SEALING COMPOSITION

(75) Inventors: Gilles Richard, Crosne (FR); Olivier Marie, Soisy sur Seine (FR)

(73) Assignee: Septodont ou Septodont SAS ou Specialites Septodont, Saint Maur des Fosses (FR)

( * ) Notice: Subject to any disclaimer, the term of this patent is extended or adjusted under 35 U.S.C. 154(b) by 160 days.

(21) Appl. No.: 13/499,902

(22) PCT Filed: Nov. 14, 2011

(86) PCT No.: PCT/EP2011/070040
§ 371 (c)(1),
(2), (4) Date: Apr. 2, 2012

(87) PCT Pub. No.: WO2012/065946
PCT Pub. Date: May 24, 2012

(65) Prior Publication Data
US 2012/0270184 A1 Oct. 25, 2012

(30) Foreign Application Priority Data
Nov. 15, 2010 (EP) .................................... 10191255

(51) Int. Cl.
| A61K 6/08 | (2006.01) |
| A61K 6/083 | (2006.01) |
| A61C 5/02 | (2006.01) |
| A61C 5/04 | (2006.01) |
| A61K 6/00 | (2006.01) |
| A61K 6/06 | (2006.01) |

(52) U.S. Cl.
CPC ............. *A61K 6/0073* (2013.01); *A61K 6/0091* (2013.01); *A61K 6/0668* (2013.01); *A61K 6/0625* (2013.01); *A61K 6/0681* (2013.01); *A61K 6/0675* (2013.01)
USPC .......... 523/117; 523/118; 433/224; 433/228.1

(58) Field of Classification Search
CPC ...... A61K 6/0038; A61K 6/06; A61K 6/0836
USPC .................... 523/117, 118; 433/224, 228.1
See application file for complete search history.

(56) References Cited

U.S. PATENT DOCUMENTS

| 2,122,011 A | 6/1938 | Schoenbeck et al. ............ 106/35 |
| 2,901,377 A | 8/1959 | Bode et al. ..................... 428/413 |
| 4,381,918 A | 5/1983 | Ehrnford et al. ............... 523/115 |
| 4,647,600 A | 3/1987 | Kawahara et al. |
| 5,584,926 A | 12/1996 | Borgholm et al. ............ 106/713 |
| 6,334,775 B2 | 1/2002 | Xu et al. ..................... 443/228.1 |
| 6,652,282 B2 * | 11/2003 | Jensen et al. ................ 433/228.1 |
| 6,858,074 B2 | 2/2005 | Anderson et al. ............. 106/724 |
| 7,819,663 B2 | 10/2010 | Bergaya et al. ............... 523/116 |
| 7,942,961 B2 * | 5/2011 | Asgary ............................ 106/35 |
| 2002/0045678 A1 | 4/2002 | Lopez et al. .................. 523/116 |
| 2002/0198283 A1 | 12/2002 | Imai et al. |
| 2003/0127026 A1 | 7/2003 | Anderson et al. ............. 106/724 |
| 2005/0025622 A1 | 2/2005 | Djeridane et al. .......... 416/97 R |
| 2006/0102049 A1 | 5/2006 | Bergaya et al. |
| 2007/0009858 A1 | 1/2007 | Hatton et al. |
| 2007/0072957 A1 * | 3/2007 | Noguchi et al. ............... 523/116 |
| 2008/0085948 A1 | 4/2008 | Primus et al. |
| 2011/0281241 A1 * | 11/2011 | Pandolfelli et al. ........... 433/224 |

FOREIGN PATENT DOCUMENTS

| CN | 1446530 A | 10/2003 |
| DE | 19923956 | 11/2000 |
| EP | 1531779 | 1/2010 |
| FR | 2603274 | 3/1988 |
| JP | 03165773 | 7/1991 |
| JP | 2003-286176 | 10/2003 |
| RU | 2197940 | 2/2003 |
| WO | 93/21122 | 10/1993 |
| WO | 01/76534 | 10/2001 |
| WO | 2004/017929 | 3/2004 |
| WO | 2005/087178 | 9/2005 |
| WO | WO 2005/087178 | 9/2005 |
| WO | 2008/000917 | 1/2008 |
| WO | 2008/100451 | 8/2008 |
| WO | 2008/100452 | 8/2008 |
| WO | 2008/102214 | 8/2008 |
| WO | WO 2008/100451 | 8/2008 |
| WO | 2013/041709 | 3/2013 |

OTHER PUBLICATIONS

English abstract of RU 2197940 C1, Feb. 10, 2003.*
Kogan el al., "The effects of various additives on setting properties of MTA," *Journal of Endodontics*, 32(6):569-572, 2006.
International Search Report dated Dec. 30, 2011, from the patent application PCT/EP2011/070040.
D. P. Bentz et al., "Effects of cement particle size distribution on performance properties of portland cemend based materials", Cement and Concrete Research, vol. 29, N°10, Oct. 1999, pp. 1663-1671.
Andreeva et al., "Mechanism of Effect of Calcium Chloride on Processes of Disperse Strcuture Formation and Chemical Intercation in Hydration of B-Dicalcium and Tricalcium Silicates", Colloids J.USSR, vol. 44, N°4, 1982, pp. 568-573.
Abstract of published Japanese Translation No. 2009-512713 of the PCT International Application, 2009.
Abstract of published Japanese Translation No. 2010-518093 of the PCT International Application, 2010.

* cited by examiner

*Primary Examiner* — Tae H Yoon
(74) *Attorney, Agent, or Firm* — Fulbright & Jaworski LLP

(57) ABSTRACT

This invention relates to a composition resulting from the mixture of a solid phase, comprising at least one calcium derivative powder in association with at least one radioopacifier and at least one polymer and optionally at least one non-radioopaque filler, all in powder form; and aqueous phase comprising water, at least one water-reducing agent, and at least one set accelerator; the ratio of solid phase to liquid phase ranging from 1.0 to 2.5, preferably from 1.5 to 2.2, more preferably from 2 to 2.15; said composition having a compressive strength of less than 40 MPa, preferably ranging from 1 to 15 MPa, preferably ranging from about 3 to about 12 MPa; this invention also relates to a kit and a method for the manufacture of the composition, and to a method for treating or retreating a canal root.

15 Claims, No Drawings

ENDODONTIC SEALING COMPOSITION

This application is a national phase application under 35 U.S.C. §371 of International Application No. PCT/EP2011/070040 filed 14 Nov. 2011, which claims priority to European Application No. 10191255.8 filed 15 Nov. 2010. The entire contents of each of the above-referenced disclosures is specifically incorporated herein by reference without disclaimer.

FIELD OF INVENTION

This invention relates to a composition for use in endodontic field. More specifically, this invention relates to improved dental compositions for endodontic treatment such as for example filling and/or permanent obturation of a root canal of a tooth.

BACKGROUND OF INVENTION

A tooth includes an upper part, referred to as the crown, made of dentin coated with enamel, and a lower part, generally referred to as pulp chamber including an upper pulp chamber and root canals that extend to the apex or apical section of the tooth into the jaw. The pulp chamber includes a living tissue, called the pulp, including blood vessels and nerves, present in the upper chamber and in the root canals. The nerves link the tooth to the general system and go to the system through little orifices of the root, called foramen.

Endodontic treatment may be needed in a number of situations well-known in the art, for example when the pulp is damaged following deep decay, traumatic injury, infection by bacteria, or after periodontal disease. Without treatment, an abscess can form at the root tip. This can lead to pain and swelling and may cause damage to surrounding bone, cementum and/or gum.

The aim of an endodontic treatment is to repair and save a tooth to avoid extraction. It includes:
- removing the damaged pulp, including the removal of inflamed or dead nerves and blood vessels from the pulp chamber, until the pulp chamber and the root canals are empty,
- cleaning and disinfecting the pulp chamber, including the root canals, after removal of possibly remaining pulp and/or mineral debris created by the endodontic instruments,
- filling and sealing the root canal and the foramen with an inert, biocompatible material.

One method for filling root canals involves using naturally occurring or synthetic Gutta Percha, an isomer of rubber. Gutta Percha points having a tapered conical shape can be prepared, and these points can be fitted into the root canal. Depending on the clinical situation, the practionner may consider appropriate—or not—the use Gutta Percha points. However, the prior art compositions are either monoblock, which means that they are supposed to be used without Gutta Percha points, and to completely fill the canal root (main canals as well as lateral and accessory canals); or the prior art compositions are monocone (or multi-cone) which means that they are supposed to be used with at least one Gutta Percha point to ensure a satisfactory sealing.

There is thus a need to provide a multi-function composition, which both provides a very good adhesion to Gutta Percha points and may be used as monocone (or multicone) composition, and may also be used as a monoblock composition without any Gutta Percha points.

In some situations, a first endodontic treatment may need to be renewed. This may happen for example in the following situations where:
- narrow or curved canals were not treated during the initial procedure,
- complicated canal anatomy went undetected in the first procedure,
- the placement of the crown or other restoration was delayed following the endodontic treatment,
- the restoration did not prevent salivary contamination to the inside of the tooth,
- new decay, or loose, cracked or broken crown causing a new infection in the tooth.

There is thus a need to provide a composition, which provides a good sealing in an endodontic first treatment (good adhesion to dentine and optionally Gutta Percha points), and which can be renewed, whatever the mode of use (with or without Gutta Percha points).

Well-known cements of the prior art are Portland cements, which are mixed with water prior to operation to form a slurry-like composition that is introduced into the root canal defect. Other cements are well-known in the prior art, among them may be cited: phenoplasts, which are phenol formaldehyde resins (PF) including synthetic thermosetting resins such as obtained by the reaction of phenols (for example resorcinol) with formaldehyde; phenoplasts are made from ingredients known to be toxic, such as for example formaldehyde, and may have further drawbacks, such as a lack of sealing overtime;
- mixtures of zinc oxide and eugenol, which lack of biocompatibility and may interact with composite restorative materials;
- epoxy resin cements, with use of Gutta Percha points, which also lack of biocompatibility;
- calcium hydroxide cements, which may not fully ensuring sealing and tightness;
- cross-linkable composition, such as cross-linkable silicons or cross-linkable thermoplastic compositions with adhesive components, which are controversial in terms of durability, sealing and toxicity issues, due to their monomers.

WO 2008/100451 discloses a composition for treating a root canal in a tooth, comprising: 1-80% of particulate material, 1-50% of a liquid phase comprising water soluble polymer, surfactant and water, the ratio of surfactant to water-soluble polymer being no greater than 6 to 1, the particulate material and liquid carrier being mixed together to form a hydrate gel material that can harden. In this document, it is emphasized that water-soluble polymer form complexes that impart desirable rheological properties to the composition.

WO 2005/087178 discloses a composite material comprising a polymer-infiltrated calcium cement, where the polymer may be polyvinylpyrrolidone, polyvinylalcohol, and the like.

Besides the fact that these prior art composition are not multifunctional, i.e. susceptible to be used with or without Gutta Percha points, they are not adapted for retreatment of the tooth, which means that they can't be easily removed from a treated tooth.

Therefore, there still remains a need for a multifunctional composition (useful both with and without Gutta Percha), easily renewed (whatever the mode of use) and biocompatible.

TECHNICAL ISSUE

However, none of the prior art documents proposes a composition ensuring both a safe sealing in an endodontic first treatment and an easy removal of the composition, with or without Gutta Percha point, in an endodontic further treatment also called retreatment procedure. On the contrary, fighting against the so-called "sand-like feel" of mineral trioxide aggregates of the prior art, one skilled in the art focused on the hardness of the final composition, making it almost impossible to retreat.

According to the Applicant, there is a remaining issue for ensuring, tight sealing of the root canal restoration on a long run.

Moreover, the prior art compositions fail to provide a composition which may be used efficiently without Gutta Percha, when needed, i.e. a composition capable to form a monoblock.

There is thus still a need for a composition having improved sealing properties, together with handling and placement properties, susceptible to be easily used with Gutta Percha points (mono- or multicone) and showing good adhesion properties to said points, and also easily used without Gutta Percha points as a monoblock, and also compatible with retreatment procedures.

There is also a need to provide a composition for root canal restoration that is compatible with the usual crown restoration materials.

The composition of the invention is of great advantage, in that it solves each above-mentioned technical issue independently, and in combination. Especially, the composition of the invention may be easily retreated, has tight sealing properties overtime (several years), is compatible with usual restorative materials, may form a monoblock when used without Gutta Percha points, and has good adhesion properties with the Gutta Percha points when used in combination to Gutta Percha points.

Especially, the composition of the invention allows a facilitated retreatment procedure. This feature may be due, not entirely but substantially, to the compressive strength of the composition of the invention: the rotary tool used for retreatment shall be directed towards the softest areas, i.e. towards the areas occupied by the less resisting material. As the composition of the invention shows limited resistance with comparison to environing dentine, the rotary tool will attack and be guided in the area occupied by the composition.

Also, the composition of the invention provides a tight seal against the root canal walls and prevents bacterial migration through the root canal. This seal is particularly tight because of the nature of the composition of the invention: the composition is manufactured through the reaction of a solid phase containing a solid calcium derivative with a liquid phase, said reaction resulting in the formation of a paste, acting as a seal composition. As the reaction, triggered by water, is not complete, it may continue whenever the composition is within a humid/moisturized environment. Consequently, even after the composition is placed and set in situ, for example in the radicular canals or close to the apical ends, it may still evolve, and the newly formed paste fills up the possibly remaining cavities and hollows.

Moreover, the composition of the invention is biocompatible and friendly to surrounding living tissues, i.e. well-supported and not inducing any inflammatory or immune processes. This feature is particularly due to the absence of aggressive components often present in prior art compositions. Especially, the composition preferably is free of epoxy-type resine, phenoplasts, acrylic derivatives, eugenol and the like.

Another advantage of the present composition is that, when used without Gutta Percha points, it forms a monoblock with strong adhesion to radicular dentin, and when used with Gutta, it forms a monocone with strong adhesion to both Gutta point and radicular dentin. It has to be noted that the composition of the invention has very limited shrinkage, and in an embodiment, does not shrink.

The composition of the invention also shows a number of further advantages over the prior art composition, in terms of working time, so that the dental practitioner can easily handle and place the composition. During working time, the composition of the invention is also very efficient because, it is sticky and has very good adhesive properties to Gutta Percha points and to radicular dentin. The composition of the invention is also very advantageous in terms of setting time, as explained below. These features may particularly be due to the ratio liquid/solid used for the mixing of the solid phase with the liquid phase.

DETAILED DESCRIPTION

The invention relates to a composition for use in the treatment of a root canal in a tooth, particularly for filling and sealing the root canal and the foramen.

This invention thus relates to a composition resulting from the mixture of a solid phase, comprising at least one calcium derivative powder in association with at least one radioopacifier and at least one polymer and optionally at least one non-radioopaque filler, all in powder form; and aqueous phase comprising water, at least one water-reducing agent, and at least one set accelerator, the ratio of solid phase to liquid phase ranging from 1.0 to 2.5, preferably from 1.5 to 2.2, more preferably from 2 to 2.15, said composition having a compressive strength of less than 40 MPa, preferably ranging from 1 to 15 MPa, preferably ranging from about 3 to about 12 MPa. Compressive strength is measured according to the protocol set forth in Example 1 below, at least 24 hours after setting time is over.

In an embodiment, said aqueous phase is free of any water-soluble polymer selected from polyvinyl alcohols, polyvinylpyrrolidone, partially hydrolyzed polyvinyl acetates, polyacrylic acid, and polymethacrylic acid, and copolymers and mixtures thereof.

Solid Phase:

Preferably, the calcium derivative powder is selected in the group comprising calcium silicate, calcium aluminate, tetracalcium aluminoferrite, calcium phosphate, calcium sulfate, silica, alumina, calcium oxide, calcium hydroxide, and mixtures thereof, preferably the calcium derivative powder is tricalcium silicate or an association of tricalcium silicate and dicalcium silicate. In an embodiment, the calcium derivative powder is present in the solid phase in an amount ranging from 30 to 80%, preferably 40 to 70%, more preferably 50 to 60% in weight to the weight of the solid phase.

The radioopacifier may be defined as a radioopacity imparting agent, which may also be considered as a radioopaque filler, and is preferably selected from the group comprising bismuth oxide, strontium carbonate, strontium phosphate, barium sulfate, tantalum oxide, cerium oxide, tin oxide, zirconium oxide compounds preferably zirconium oxide in combination with yttrium and radioopaque glasses containing tantalum, barium and strontium, and mixtures thereof, preferably, the radioopacity imparting component is bismuth derivatives, such as for example bismuth oxides or bismuth carbonates or mixture thereof, or zirconium derivatives, especially zirconium oxide alone or in combination with yttrium; or a mixture of bismuth derivatives and zirconium derivatives. In an embodiment, the radioopacifier is present in the solid phase in an amount ranging from 1 to 50%, preferably from 10 to 40%, more preferably from 13 to 35% in weight to the weight of the solid phase.

In a preferred embodiment, the polymer is selected from the group comprising polyvinyl alcohols, polyvinyl-pyrrolidone (PVP), partially hydrolyzed polyvinyl acetates, (PVAc), polyacrylic acid (PAA), polymethacrylic acid (PMA), acrylic based polymers, functionalized silicones, alginates and non-water soluble polymers, and copolymers and mixtures thereof. In an embodiment, the polymer is present in the solid phase in an amount ranging from 1 to 20%, preferably from 3 to 10%, more preferably about 5% in weight to the weight of the solid phase.

In an embodiment, the non-radioopaque filler is at least one calcium derivative, such as for example calcium phosphate, carbonated calcium phosphates, calcium carbonate. The filler, especially calcium carbonate, may also be a set accelerator. In an embodiment, the filler is present in the solid phase in an amount of less than 50%, preferably less than 40%, more preferably in an amount ranging from 0 to 30% even more preferably, when present, in an amount ranging from 12 to 22% in weight to the weight of the solid phase.

Liquid Phase:

In an embodiment, the water-reducing agent is an agent improving the rheological properties of the composition, and may behave as a plastifying or fluidifying agent. Preferably, the water-reducing agent is selected from the group comprising polycarboxylate and a modified polycarboxylate, preferably a polymethyl acrylic acid esterified with ethylene polyoxide chains. Among these compounds are preferred poly (meth)acrylates of polyhydric alcohol, polyallyl ethers of polyhydric alcohol, and polyallyl polycarboxylates, in view of radical polymerization rate. More preferred are trimethylolpropane tri(meth)acrylates, pentaerythritol tetra(meth) acrylates and dipentaerythritol penta(meth)-acrylates; among which especially preferred are these acrylates, particularly dipentaerythritol pentaacrylate (hereinafter referred to as DPPA). In an embodiment, the water-reducing agent is present in the liquid phase in an amount ranging from 5 to 15%, preferably from 6 to 10%, more preferably about 8% in weight to the weight of the liquid phase. In another embodiment, the water-reducing agent is present in the liquid phase in an amount ranging from 0.1% to less than 5%, preferably from about 0.5% to about 4%, more preferably about 1% to about 3% in weight to the weight of the liquid phase In an embodiment, the set accelerator is calcium chloride. Preferably, the set accelerator is present in the liquid phase in an amount ranging from 10 to 50%, preferably from 20 to 40%, more preferably about 30% in weight to the weight of the liquid phase.

In an embodiment, the liquid phase includes water in an amount ranging from 50 to 85%, preferably 60 to 70% in weight to the weight of the liquid phase.

Features of the Composition after Mixing

According to an embodiment of the invention, the working time of the composition ranges from 5 to 80 minutes, preferably from 6 to 60 minutes, more preferably from about 30 to 40 minutes.

According to an embodiment, the composition presents a creamy consistence and is sticky during working time, resulting in a strong adhesion to instruments, eventually Gutta Percha points, and radicular dentin. According to an embodiment of the invention, the flow of the composition is more than 20 mm, preferably more than 22 mm, even more preferably about 23 mm.

The sealing properties of the composition of the invention may result from the adhesion of its adhesion with the radicular dentine. This invention presents a further advantage that the sealing does not degrade overtime.

According to an embodiment of the invention, the setting time of the composition ranges from 40 minutes to 30 hours, preferably from 60 minutes to 23 hours, more preferably from 7 to 20 hours. According to a particular embodiment, the composition of the invention matches with the specification of the ISO standard ISO6876, related to Dental root canal sealing materials. ISO6876 requires a setting time ranging from 30 minutes to 72 hours.

According to an embodiment, the composition of the invention undergoes limited dimensional changes following setting. In a preferred embodiment, the dimensional change following setting is less than 1% shrinkage, more preferably less than 0.1%. In an embodiment, the composition of the invention does not shrink.

According to an embodiment, the composition has a radioopacity ranging from 2.5 to 15, preferably from 4 to 10, even more preferably from 4.5 to 9.5 mm Aluminium. This range of radioopacity allows the easy detection of the composition when administered to a tooth, and thus facilitate the control of a tooth treatment. According to a particular embodiment, the composition of the invention matches with the specification of ISO6876.

According to an embodiment of the invention, the film thickness of the composition is less than 50 μm, preferably less than 45 μm, more preferably about 43 μm. According to a particular embodiment, the composition of the invention matches with the specification of ISO6876, which requires a film thickness inferior to 50 μm.

In a first embodiment, the composition of the invention is for use without Gutta Percha point, i.e. as a monoblock.

In a second embodiment, the composition of the invention is for use with one or more Gutta Percha point, i.e. respectively as monocone or multicone.

In a preferred embodiment of the invention, the composition is for use with no more than one Gutta Percha points.

In a preferred embodiment of the invention, the composition allows the complete filling of the canal root of a tooth, whatever the mode of use (monoblock, monocone or multicone).

In an embodiment of the invention, the composition of the invention can be easily retreated, for example by means of rotary tools, whatever the mode of use (monoblock, monocone or multicone) of the preceding treatment. In an embodiment of the invention, the composition presents a low mechanical resistance, which facilitates the retreatment.

Kit of Parts

This invention also relates to a kit for the preparation of a composition of the invention, comprising in a first container, a solid phase, comprising at least one calcium derivative powder in association with at least one radioopacifier and a polymer and optionally at least one non-radioopaque filler, all in powder form; and in a second container, an aqueous phase comprising water, at least one water-reducing agent, and at least one set accelerator; said first and second containers being designed for the mixing the solid phase to liquid phase in a ratio solid/liquid ranging from 1.0 to 2.5, preferably from 1.5 to 2.2, more preferably from 2 to 2.15.

Manufacturing Process

This invention also relates to a method for manufacturing a composition of the invention for treating a root canal in a tooth, comprising mixing a solid phase, comprising a calcium derivative powder in association with a radioopacifier and a polymer and optionally a non-radioopaque filler, all in powder form; and aqueous phase comprising water, a water-reducing agent, and a set accelerator, the ratio of solid phase to liquid phase ranging from 1.0 to 2.5, preferably from 1.5 to 2.2, more preferably from 2 to 2.15, said composition having a compressive strength of less than 40 MPa, preferably ranging from 1 to 15 MPa, preferably ranging from about 3 to about 12 MPa.

In one embodiment of the invention, the method of the invention further comprises the fitting of one or more Gutta Percha point into the root canal. In a preferred embodiment of the invention, no more than one Gutta Percha is fitted into the root canal.

Composition for Use in the Treatment or Retreatment of a Canal Root and Method for Treating or Retreating a Canal Root This invention also relates to a composition for use in the treatment or retreatment of a canal root and method for treating or retreating a canal root, wherein the composition of the invention is used for filling the root canal.

DEFINITIONS

In the present invention, the following terms have the following meanings:

"About" means plus or minus ten percent of the number, parameter or characteristic so qualified.

"Biocompatibility" refers to a biomaterial eliciting little or no immune response in a given organism, or is able to integrate with a particular cell type or tissue.

"Radioopacity" refers to substance that will not allow X-rays or similar radiation to pass.

"Polymer" refers to a large molecule formed by the repetition of a structural unit. According to the invention, the polymer may be a water soluble polymer or a water immiscible polymer. In the kit of the invention, the polymer is in powder form, in the solid phase.

"Set accelerator" refers to an agent which reduces the setting time of a material when added to said material.

"Fluidifying agent" refers to an agent which, when added to a physical substance, enhances the fluidity of said substance by reducing the attracting strength between the particles constituting said substance.

"Plastifying agent" refers to an agent, in a powder form and insoluble, which, when added to a substance, enhances the viscosity and the cohesion of said substance.

"Working time" refers to the period of time measured from the start of mixing during which it is possible to manipulate the composition of the invention, according to the criteria and conditions described in 7.3 of ISO 6876/2001, without any adverse effect on its properties.

"Setting time" refers to the period of time measured from the end of mixing until the composition of the invention has set, according to the criteria and conditions described in 7.4 of ISO 6876/2001.

The invention will be further illustrated by the compositions described in the following examples, which should not in any way be construed as limiting the scope of the invention

EXAMPLES

Compositions 1-10

Compositions 1 to 10 were designed as reported below.

Mixtures were performed on a w/w ratio solid phase to liquid phase of 1.0 to 2.5, preferably from 1.5 to 2.2, more preferably from 2 to 2.15.

|  | Ingredient/Composition # | 1 | 2 | 3 | 4 | 5 | 6 | 7 | 8 | 9 | 10 |
|---|---|---|---|---|---|---|---|---|---|---|---|
| Solid phase | C3S or mixture C3S/C2S | 60 | 60 | 60 | 60 | 60 | 60 | 60 | 50 | 60 | 60 |
|  | Calcium carbonate | 22 | 22 | 12 |  | 22 |  |  | 15 |  |  |
|  | Bismuth Oxide | 13 |  | 13 | 13 |  |  | 35 |  |  |  |
|  | Zirconium oxide + Yttrium |  |  |  |  | 13 | 35 |  | 30 |  |  |
|  | Zirconium oxide |  |  |  |  |  |  |  |  |  | 35 |
|  | Strontium carbonate |  | 13 | 10 | 22 |  |  |  |  | 35 |  |
|  | PVP | 5 | 5 | 5 | 5 | 5 | 5 | 5 | 5 | 5 | 5 |
| Liquid phase | Water |  |  |  |  | 62.6 |  |  |  |  |  |
|  | Modified polycarboxylate |  |  |  |  | 8 |  |  |  |  |  |
|  | CaCl2 |  |  |  |  | 29.4 |  |  |  |  |  |

Amounts are given in weight to the total weight of the phase.

The composition of the invention has the following features:

| Composition # | 1 | 2 | 3 | 4 | 5 | 6 | 7 | 8 | 9 | 10 |
|---|---|---|---|---|---|---|---|---|---|---|
| Working time | 30-40 mn | 13-25 mn | 25-40 mn | 6-10 mn | 10-25 mn | 15-25 mn | 30-40 mn | 15-50 mn | 25-60 mn | 30-35 mn |
| Setting time | 60-90 mn | 90-230 mn | 3-23 h | 5-22 h | 2-19 h | 6-18 h | 7-18 h | 2-4 h | 7-20 h | 7-20 h |
| Radiopacity (mm) | 3 | 3-3.5 | 2.7-4 | 3.5-6.5 | 2.5-4.5 | 3 | 4.8 | 3 | 3.3 | 5 |
| Compressive strength at 24 h (Mpa) | 10.1 | 9.9 | 7.4 | 3.5 | 8.1 | 11.7 | 8 | 9.3 | 10.8 | 7.6 |

Description of Compressive Strength Test:

Compressive strength is a classical mechanical evaluation of the dental biomaterials (ISO 9917:1991). Specimens were mixed at room temperature, according to each manufacturer's instructions. 6 specimens were prepared using cylindrical Teflon moulds, 4 mm in diameter and 6 mm long, removing air bubbles. Specimens were stored in an incubator for 15 minutes in 100% relative humidity (dry) with 37° C. and then removed from the mould and stored (wet) in distilled water at 37° C., for the remaining time (simulation of the clinical application).

Preclinical Tests
First Preclinical Evaluation:

Endodontic curves simulators were prepared in resin. They are shaped according to usual endodontic treatment needs. They were filled with compositions 1-10 either in monoblock, or in mono-cone, and were then emptied using rotary instruments after hardening of the composition Results:

The spooning of the composition does not present any difficulty. An immediate coloration of the mixture in grey is observed during the application with a metallic spatula, which is not found when the spatula is made of thermoplastic material.

The filling with the composition, using a lentulo, leads to a complete filling of the volume with a weak extrusion of composition. The filling by coating walls using a lentulo followed by the insertion of a gutta-percha cone also leads to a complete filling of the volume with a weak extrusion of composition.

The removal of the composition at 24 hours does not raise any problem whatever mode of use is carried out, i.e. monoblock or mono-cone. Removal is easily realized without deviation of the trajectory of the root canal.

The removal of the composition carried out at 72 hours showed the following:
  Root canals filled with the composition in mono-block can be emptied by means of rotary instruments,
  Root canals filled with a Gutta-Percha cone sealed with the composition are easily emptied with an excellent preservation of the trajectory of the root canal (probably because of the properties of the composition which prevents the deviation of the rotary instrument and would play guide's role).

The removal of the composition carried out at 7 days showed the following:
  Monocone: removal is easy, the cone was perfectly adapted to the shape of the canal while not adhering to the walls
  Monoblock: removal is quick and easy, mechanical properties of the composition are well-adapted to retreatment.

Second Preclinical Evaluation:

Single-curve and double-curve endodontic simulators were filled with the composition, used as a sealing composition, with one of the following techniques: mono-cone or Thermafil (in comparison with the cement BC sealer from Enclosequence [comparison] and the Top Seal resin from Dentsply-Maillefer [control]).

The use of the composition is not adapted to the implementation of a technique of filling with a warm gutta-percha (technique of Schilder or System B), because the heat exceeds 200° C.

Results:

Trials for setting up the Thermafil prop at the needed length were unsuccessful when cement BC was used (utilized according to the protocol of the manufacturer), due to the presence of a column of cement excessive in size. The complete insertion of a classical gutta-percha cone (i.e. different from that recommended for this technique) also raised issues due to the lack of rigidity of the gutta-percha cone. Using the composition, the set up of the gutta-percha cone at the needed length, was made possible, and even easy, in single curve canals as well as in double curve canals, being emphasized that the preferred technique was the coating of walls with a lentulo followed by insertion of Gutta (by comparison with the technique of complete filling with the lentulo followed by the insertion of the gutta-percha cone).

Trials for setting up the Thermafil prop at the needed length were successful after a thin coating of walls with composition was performed and after removal of excess (same protocol than for the implementation of the resin Top Seal).

The invention claimed is:

1. A composition comprising:
  a solid phase comprising at least one calcium derivative, at least one radioopacifier, and at least one polymer;
    wherein said at least one calcium derivative is selected from one or more of: calcium silicate, calcium aluminate, tetracalcium aluminoferrite, calcium phosphate, calcium sulfate, calcium oxide, and calcium hydroxide;
    wherein said at least one radioopacifier is selected from one or more of: bismuth oxide, bismuth carbonate, yttrium, strontium carbonate, strontium phosphate, barium sulfate, tantalum oxide, cerium oxide, tin oxide, a zirconium oxide compound, and a radioopaque glass containing one or more of tantalum, barium, and strontium;
    wherein said at least one polymer is selected from one or more of: polyvinyl alcohol, polyvinyl-pyrrolidone (PVP), partially hydrolyzed polyvinyl acetate (PVAc), polyacrylic acid (PAA), polymethacrylic acid (PMA), acrylic based polymer, alginate, and non-water soluble polymer;
    wherein said at least one calcium derivative, said at least one radioopacifier, and said at least one polymer are present in an amount ranging from 30 to 80%, 1 to 50%, and 1 to 20% in weight to the weight of the solid phase; and
  an aqueous phase comprising water, at least one water-reducing agent, and at least one set accelerator;
    wherein said at least one water-reducing agent is selected from one or more of: polycarboxylate and a modified polycarboxylate; and
    wherein said water, said at least one water-reducing agent and said at least one set accelerator are present in an amount respectively ranging from 50 to 85%, 5 to 15% and 10 to 50% in weight of the weight of the liquid phase; and
wherein the ratio of solid phase to liquid phase is from 1.0 to 2.5 and,
wherein the composition has a compressive strength from about 1 to about 15 MPa after setting.

2. The composition of claim 1, wherein the solid phase further comprises at least one non-radioopaque filler.

3. The composition of claim 1, wherein the calcium derivative powder comprises tricalcium silicate and/or dicalcium silicate.

4. The composition of claim 1, wherein the radioopacifier comprises bismuth oxide, bismuth carbonate or a zirconium oxide compound.

5. The composition of claim 1, wherein the radioopacifier comprises bismuth oxide, bismuth carbonate, zirconium oxide, or yttrium.

6. The composition of claim 1, having a radioopacity ranging from 2.5 to 15 mm Aluminum.

7. The composition of claim 2, wherein the non-radioopaque filler comprises calcium.

8. The composition of claim 7, wherein the non-radioopaque filler comprises calcium phosphate, carbonated calcium phosphate, or calcium carbonate.

9. The composition of claim 1, wherein the water-reducing agent is a plastifying agent or a fluidifying agent.

10. The composition of claim 9, wherein the water-reducing agent comprises a polymethyl acrylic acid esterified with ethylene polyoxide chains.

11. A method for treating or retreating a root canal comprising: obtaining a composition of claim 1; and filling the root canal with the composition.

12. The method of claim 11, wherein the composition is used as a monoblock.

13. The method of claim 11, wherein the composition is associated with at least one Gutta Percha point.

14. The method of claim 13, wherein the composition is associated with more than one Gutta Percha point.

15. A kit for the preparation of the composition of claim 1 comprising:
- a first container comprising an amount of a solid phase comprising at least one calcium derivative, at least one radioopacifier, and at least one polymer; and
- a second container comprising an amount of an aqueous phase comprising water, at least one water-reducing agent, and at least one set accelerator;

wherein the amounts of solid phase and liquid phase allow the composition to have a ratio of solid phase to liquid phase of from 1.0 to 2.5 upon mixing during use.

\* \* \* \* \*